US010293129B2

(12) United States Patent
Fox et al.

(10) Patent No.: US 10,293,129 B2
(45) Date of Patent: May 21, 2019

(54) APPARATUS AND METHOD FOR FORMING AN OPENING IN PATIENT'S TISSUE

(71) Applicant: HANSA MEDICAL PRODUCTS, INC., Carmel, IN (US)

(72) Inventors: Dart A. Fox, Indianapolis, IN (US); Eric D. Blom, Carmel, IN (US); Brian Kamradt, Indianapolis, IN (US)

(73) Assignee: HANSA MEDICAL PRODUCTS, INC., Carmel, IN (US)

( * ) Notice: Subject to any disclaimer, the term of this patent is extended or adjusted under 35 U.S.C. 154(b) by 66 days.

(21) Appl. No.: 15/452,323

(22) Filed: Mar. 7, 2017

(65) Prior Publication Data
US 2017/0252526 A1 Sep. 7, 2017

Related U.S. Application Data

(60) Provisional application No. 62/304,756, filed on Mar. 7, 2016, provisional application No. 62/364,812, filed on Jul. 20, 2016.

(51) Int. Cl.
A61B 17/00 (2006.01)
A61B 17/34 (2006.01)
(Continued)

(52) U.S. Cl.
CPC ..... A61M 16/0472 (2013.01); A61B 17/3403 (2013.01); A61B 17/3496 (2013.01); A61B 2017/00026 (2013.01); A61B 2017/00128 (2013.01); A61B 2017/00734 (2013.01); A61B 2017/3409 (2013.01);
(Continued)

(58) Field of Classification Search
CPC ............ A61B 17/3494; A61B 17/3496; A61B 17/3403; A61M 16/0472; A61F 11/002
See application file for complete search history.

(56) References Cited

U.S. PATENT DOCUMENTS 4,321,926 A 3/1982 Roge
5,217,005 A 6/1993 Weinstein
(Continued)

FOREIGN PATENT DOCUMENTS

JP 08542 A 1/1996
WO 2014088904 A1 6/2014

OTHER PUBLICATIONS

"LM Linear Probes—User's Guide", Bioanalytical Systems, Inc., Retrieved from Online on Aug. 28, 2016 (Aug. 28, 2016); Retrieved from URL: https://www.basinc.com/assets/library/manuals/lmlp.pdf, 4 pages.
(Continued)

Primary Examiner — Wade Miles
(74) Attorney, Agent, or Firm — Barnes & Thornburg LLP

(57) ABSTRACT

A surgical instrument system for use in a surgical procedure is disclosed. The surgical instrument system may include an instrument configured to puncture the tissue of a patient and detect when the instrument has entered a lumen of the patient's body. Liquid may be present in the lumen or the lumen may be devoid of liquid or tissue. The instrument is configured to determine when the needle tip is engaged with a portion of patient's tissue and determine when the needle tip has exited that portion of the patient's tissue by detecting changes in properties of the tissue, specifically, electrical resistance.

20 Claims, 10 Drawing Sheets

(51) Int. Cl.
*A61B 90/00* (2016.01)
*A61M 16/04* (2006.01)

(52) U.S. Cl.
CPC ............... *A61B 2090/0807* (2016.02); *A61M 2205/3327* (2013.01); *A61M 2205/3569* (2013.01); *A61M 2205/50* (2013.01); *A61M 2205/8206* (2013.01)

(56) References Cited

U.S. PATENT DOCUMENTS

| | | | |
|---|---|---|---|
| 5,335,668 A | 8/1994 | Nardella | |
| 5,353,800 A | 10/1994 | Pohndorf et al. | |
| 5,383,465 A * | 1/1995 | Lesny | A61B 8/0833 600/461 |
| 5,421,821 A | 6/1995 | Janicki et al. | |
| 5,423,796 A * | 6/1995 | Shikhman | A61B 17/3494 604/164.08 |
| 5,429,636 A * | 7/1995 | Shikhman | A61B 17/3494 604/164.08 |
| 5,460,182 A * | 10/1995 | Goodman | A61B 5/0084 600/342 |
| 5,496,313 A * | 3/1996 | Gentelia | A61B 17/3494 604/164.08 |
| 5,653,230 A | 8/1997 | Ciaglia et al. | |
| 5,800,350 A | 9/1998 | Coppleson et al. | |
| 6,337,994 B1 | 1/2002 | Stoianovici et al. | |
| 6,466,817 B1 | 10/2002 | Kaula et al. | |
| 6,471,659 B2 | 10/2002 | Eggers et al. | |
| 6,603,997 B2 | 8/2003 | Doody | |
| 6,760,616 B2 | 7/2004 | Hoey et al. | |
| 6,962,587 B2 | 11/2005 | Johnson et al. | |
| 7,419,487 B2 | 9/2008 | Johnson et al. | |
| 8,034,049 B2 | 10/2011 | Odom et al. | |
| 8,374,673 B2 | 2/2013 | Adcox et al. | |
| 8,696,697 B2 | 4/2014 | Blom et al. | |
| 8,838,206 B2 | 9/2014 | Mohajer | |
| 2008/0091227 A1 | 4/2008 | Schmitz et al. | |
| 2012/0004535 A1 | 1/2012 | Mohajer | |
| 2012/0180787 A1 | 7/2012 | Bosel | |
| 2012/0209167 A1 | 8/2012 | Weber et al. | |
| 2014/0303494 A1 | 10/2014 | Janicki et al. | |
| 2015/0011853 A1 | 1/2015 | Frohlich et al. | |
| 2016/0206842 A1 | 7/2016 | Blom et al. | |

OTHER PUBLICATIONS

Kalvoy et al., "Impedance-based tissue discrimination for needle guidance", Physiol. Meas. 30 (2009), pp. 129-140.

Desyatnikova et al., "Tracheosophageal Puncture in the Office Setting with Local Anesthesia", Annals of Ontology, Rhineology and Laryngology, 110, 613-616, 2001.

Koch, "A Failsafe Technique for Tracheoesphageal Puncture", The Laryngoscope, 111, Sep. 2001.

Trebbels et al., "Real-Time Cannula Navigation in Biological Tissue with high temporal and spatial resolution based on Impedance Spectroscopy", 32nd Annual International Conference of the IEEE EMBS, Aug. 31-Sep. 4, 2010, 4 pages.

Blom-Singer® Voice Prosthesis Placement Surgical Kit available from Inhealth® Technologies.

International Search Report and Written Opinion, International Application No. PCT/US2016/013528, search completed Apr. 19, 2016, 14 pages.

Kalvoy, "Needle Guidance in Clinical Applications based on Electrical Impedance", Oslo University Hospital, Department of Clinical and Biomedical Engineering, Rikshospitalet, Oslo University Hospital Norway, 2010, 82 pages.

* cited by examiner

APPARATUS AND METHOD FOR FORMING AN OPENING IN PATIENT'S TISSUE

This application claims priority to U.S. Patent App. Ser. No. 62/304,756, which was filed on Mar. 7, 2016, and U.S. Patent App. Ser. No. 62/364,812, which was filed on Jul. 20, 2016, the entireties of each of which are expressly incorporated herein by reference.

CROSS-REFERENCE TO RELATED APPLICATIONS

Cross-reference is made to U.S. patent application Ser. No. 14/996,426, which was filed on Jan. 15, 2016, and International Application No. PCT/US16/13528, which was filed on Jan. 15, 2016. Each of those applications is expressly incorporated herein by reference.

TECHNICAL FIELD

The present disclosure relates to instruments for forming and dilating an opening in a patient's tissue and, more specifically, for dilating an opening through a tracheal wall of a patient.

BACKGROUND

There are a number of techniques for establishing an adequate air passageway for a patient. When the trachea, nostrils and/or mouth are free of obstruction, endotracheal intubation, which involves the insertion of a tube through the nostrils or mouth and into the trachea itself, may be used. One endotracheal tube system for use in endotracheal intubation is described in International Patent Application Publication No. WO2014/088904, which is incorporated herein by reference.

Another technique for establishing an adequate air passageway involves the creation of a puncture or incision in the tracheal wall. A tracheostomy tube may then be inserted through the opening to form a passageway that effectively bypasses the upper trachea, nostrils and/or mouth. The initial incision may be made with a smaller needle and then enlarged or dilated to receive the tracheostomy tube.

Various techniques and devices for creating punctures or other incisions in the soft issue of a patient are illustrated and described in: "An Endoscopic Technique for Restoration of Voice After Laryngectomy," Annals of Ontology, Rhinology And Laryngology, Singer et al., 89: 529-533, 1980, "Tracheoesophageal Puncture," Atlas of Transnasal Esphagoscopy," Postma, et al., 2007, Tracheoesophageal Puncture in the Office Setting with Local Anesthesia, Annals of Ontology, Rhinology And Laryngology, Desyatnikova et al., 110, 613-616, 2001, A Failsafe Technique For Tracheoesophagal Puncture, Koch, The Laryngoscope, 111, September 2001, A New Method For Tracheoesophagal Puncture Under Topical Anesthesia, Gross et al., The Laryngoscope, 104, February 1994, and the Blom-Singer® Voice Prosthesis Placement Surgical Kit available from Inhealth® Technologies. Another device for use with the soft tissue of a patient is the BD Angiocath Autoguard Shielded IV Catheter, which is commercially available from Becton, Dickinson and Company of New Jersey.

There are also the devices and methods illustrated and described in U.S. Pat. Nos. 5,653,230; 5,217,005; and 8,696,697; and U.S. Pat. App. Pub. No. 2012/0180787. The disclosures of these references are hereby incorporated herein by reference. Another device and method is shown in U.S. Pat. No. 6,603,997. This listing is not intended as a representation that a complete search of all relevant prior art has been conducted, or that no better references than those listed exist.

SUMMARY

According to one aspect, a surgical instrument system comprises a housing including a handle, a shaft extending outwardly from the housing to a distal end configured to form a puncture in a patient's tissue, a conductor plate positioned in the shaft, a retraction mechanism operable to move the distal end of the shaft in a first direction toward the housing, and a controller positioned in the housing. The controller is configured to energize a sensor circuit including a section of the shaft and the conductor plate, and monitor an electrical signal received from the sensor circuit. When an electrical resistance value based on the monitored electrical signal is greater than a predetermined threshold, the controller is configured to activate an indicator, and energize the retraction mechanism to move the distal end of the shaft in a direction toward the housing.

In some embodiments, the predetermined threshold for the resistance value may be greater than or equal to 100 kilo-ohms.

In some embodiments, the conductor plate may be positioned in an opening defined in the distal end of the shaft. Additionally, in some embodiments, the conductor plate may be a metallic inner shaft positioned in a passageway defined in the outer shaft.

In some embodiments, the system may comprise a non-conductive film positioned in the opening defined in the distal end of the shaft between the conductor plate and the shaft that electrically isolates the conductor plate from the shaft. Additionally, in some embodiments, the non-conductive film may include an annular ring that surrounds the conductor plate. In some embodiments, the non-conductive film may include a cylindrical ring that is positioned in a passageway defined in the outer shaft between a metallic inner shaft of the conductor plate and the outer shaft. In some embodiments, the annular ring or cylindrical ring may have a thickness of 0.5 millimeters. The non-conductive film may be formed from a non-conductive plastic or silicone material.

In some embodiments, the indicator is a visual indicator. Additionally, in some embodiments, the controller may be configured to determine whether the distal end has engaged tissue of a patient based on the electrical signal received from the sensor circuit, energize the indicator in a first state when the controller has determined that the distal end has engaged tissue of the patient, and energize the indicator in a second state to activate the indicator when the controller has determined that the distal end has penetrated the lumen of the patient. In some embodiments, the second state is different from the first state such that a user may determine whether the instrument is armed and/or has penetrated the lumen.

In some embodiments, when the resistance value based on the monitored electrical signal is less than a predetermined value for a predetermined period of time, the controller may be configured to energize the indicator in a first state to indicate the instrument is armed. Additionally, in some embodiments, the predetermined value may be in a range of 1 kilo-ohm to 100 kilo-ohms In some embodiments, the predetermined period of time may be equal to 200 milliseconds. Additionally, in some embodiments, the instrument may include a switch operable to be toggled by a user to disarm the instrument.

In some embodiments, the first state may be one of a flashing light and a continuous light, and the second state may be the other of a flashing light and a continuous light. It should be appreciated that in some embodiments the first state may include flashing the indicator at a first frequency, and the second state may include flashing the indicator at a second frequency different from the first frequency.

In some embodiments, the retraction mechanism may include a linear actuator that is electrically-operated. Additionally, in some embodiments, the shaft may be operable to move along a first axis, and the linear actuator may be operable to move along a second axis extending orthogonal to the first axis to cause the shaft to move along the first axis.

In some embodiments, the shaft may extend from the distal end to a proximal end positioned in the housing, and the retraction mechanism includes a mounting frame secured to the proximal end of the shaft.

Additionally, in some embodiments, the retraction mechanism may include a locking arm operable to rotate about a pivot pin between a first position in which a proximal end of the mounting frame is engaged with a first surface of the locking arm and a second position in which the proximal end of the mounting frame is received in a passageway defined in the shaft. In some embodiments, the linear actuator is operable to advance into contact with the locking arm to cause the locking arm to rotate between the first position and the second position.

In some embodiments, the retraction mechanism may further comprise a biasing element attached to an end of the locking arm, and the biasing element may be operable to bias the locking arm in the first position.

In some embodiments, the mounting frame may include a mounting bracket that has a first end secured to the shaft and a second, opposite end secured to an elongated rod, and the elongated rod may include the proximal end of the mounting frame.

In some embodiments, the locking arm may include a sleeve that includes the first surface. Additionally, in some embodiments, retraction mechanism may further comprise a biasing element operable to urge the shaft in the first direction, and the biasing element may be positioned between a plate of the mounting frame and a wall of the housing.

According to another aspect, a method for performing a surgical procedure is disclosed. The method includes inserting a needle tip of a surgical instrument into a patient's tissue, advancing the needle tip through the tissue, monitoring an indicator of the surgical instrument while advancing the needle tip through the tissue, and maintaining a position of the surgical instrument in response to the indicator indicating the needle tip has entered a target lumen of the patient.

In some embodiments, the surgical instrument may be operable to automatically retract the needle tip when the needle tip has entered the target lumen of the patient. Additionally, in some embodiments, the surgical instrument may include a control circuit operable to measure a change in electrical resistance to determine when the needle tip has entered the target lumen of the patient and activate the indicator to indicate the needle tip has entered a target lumen of the patient.

According to another aspect, a method of performing a surgical procedure comprises energizing a sensor circuit of a surgical instrument including a needle tip configured for insertion into a patient's tissue, monitoring an electrical signal received from the sensor circuit, energizing an indicator in a first state when a resistance value based on the electrical signal is less than a predetermined value corresponding to the needle tip being positioned in the patient's tissue, energizing the indicator in a second state when the resistance value based on the electrical signal is greater than a predetermined threshold corresponding to the needle tip being positioned in a patient's lumen, and energizing a retraction mechanism of the surgical instrument to move the needle tip away from the patient's lumen.

In some embodiments, the method may further comprising activating a timer when the resistance value based on the electrical signal is less than a predetermined value. The step of energizing the indicator in the first state may include energizing the indicator in the first state after a predetermined amount of time has elapsed from the activation of the timer.

In some embodiments, the method may further include activating a timer when the resistance value based on the electrical signal is greater than a predetermined threshold. The step of energizing the retraction mechanism of the surgical instrument may include energizing the retraction mechanism of the surgical instrument after a predetermined amount of time has elapsed from the activation of the timer.

Additionally, in some embodiments, the surgical instrument may include an elongated shaft, and the sensor circuit may include a portion of the shaft and a conductor plate or shaft positioned in the shaft. In some embodiments, the sensor circuit may include a pair of conductor plates, and the elongated shaft may be formed from a non-conductive material.

According to another aspect of the disclosure, a surgical instrument system for detecting a lumen in a patient's body is disclosed. When the instrument determines that the needle tip has entered the target lumen, the instrument may then activate an indicator such as, for example, a flashing light emitting diode (LED) in the instrument to alert the operator to not advance further. In one embodiment, the instrument may also be programed to instantaneously retract its tip a distance of, for example, about 8 mm In other embodiments, the tip of the instrument may remain stationary to facilitate fluid infusion or suction. In some embodiments, the system may include a noncompliant dilation balloon on a catheter for use in procedures such as, for example, percutaneous tracheostomy or percutaneous gastrostomy. In some embodiments, the surgical instrument may be another cutting tool such as, for example, a cutting blade in which the entire blade but a portion of the cutting edge may be insulated.

According to another aspect, a method for performing a surgical procedure comprises inserting a needle tip of a surgical instrument into a patient's tissue, advancing the needle tip through the tissue, monitoring an indicator of the surgical instrument while advancing the needle tip through the tissue, and maintaining a position of the surgical instrument in response to the indicator indicating the needle tip has entered a target lumen of the patient.

Illustratively according to this aspect, the surgical instrument may be operable to automatically retract the needle tip when the needle tip has entered the target lumen of the patient.

According to another aspect, a method for performing a surgical procedure comprises energizing an indicator of a surgical instrument to provide a first indication to a user when a needle tip is engaged with a portion of patient's tissue and energizing the indicator to provide a second indication different from the first indication in response to the needle tip exiting the portion of the patient's tissue.

Illustratively according to this aspect, the method may further comprise automatically retracting the needle tip in response to the needle tip exiting the portion of the patient's tissue.

Illustratively according to this aspect, energizing the indicator to provide the second indication different from the first indication in response to the needle tip exiting the portion of the patient's tissue includes energizing the indicator when the needle tip has entered the target lumen of the patient.

Illustratively according to this aspect, energizing the indicator to provide the second indication different from the first indication in response to the needle tip exiting the portion of the patient's tissue includes energizing the indicator when the needle tip has entered another portion of the patient.

According to another aspect, a dilation instrument system is disclosed. The dilation instrument system includes a percutaneous dilation balloon and a moveably positionable retainer. The percutaneous dilation balloon is included in a balloon catheter configured to be positioned in an opening defined in a tracheal wall of a patient. The catheter includes a sheath having a proximal end and a distal end, the balloon extending over the sheath between the proximal end and the distal end, and a deflectable retention flange secured to the distal end of the sheath. The retainer is positioned over the balloon and is configured to move relative to the balloon such that upon inflation of the balloon when the balloon is positioned in the opening in the tracheal wall, the retainer engages the tracheal wall to inhibit movement of the balloon catheter.

According to another aspect, a dilation instrument system comprises a percutaneous dilation balloon, a stationary deflectable retention flange, and a moveably positionable retainer. The retainer is positioned over the balloon and is configured to move relative to the balloon such that upon inflation of the balloon when the balloon is positioned in an opening in a wall of the patient's tissue, the retainer is positioned adjacent to the wall to inhibit movement of the balloon catheter.

In some embodiments, the inflatable balloon may have a maximum diameter when inflated, and the retainer may include an annular body having an inner diameter that is less than the maximum diameter of the inflatable balloon. Additionally, in some embodiments, the annular body may include a first collar extending in a first direction, a second collar extending outwardly in a second direction opposite the first direction, and a passageway extending between an opening defined in the first collar and an opening defined in the second collar. The passageway may define the inner diameter of the annular body.

In some embodiments, the sheath may comprise a tip positioned at the distal end and that is formed from a first material. The sheath may comprise an elongated body extending from the tip to the proximal end. The elongated body may be formed from a second material that is harder than the first material.

In some embodiments, the dilation instrument system may further comprise a surgical instrument configured to be coupled to the balloon catheter. The surgical instrument may comprise an elongated shaft sized to be positioned in a lumen defined in the sheath and a needle tip configured to puncture the tracheal wall. The needle tip may be configured to extend outwardly from the distal end of the sheath when the surgical instrument is coupled to the balloon catheter.

In some embodiments, the surgical instrument of the dilation instrument system may further comprise a handle coupled to the elongated shaft, an indicator including a light source in the handle, and a sensor operable to energize the light source when the needle tip penetrates a lumen of the patient's trachea.

In some embodiments, the surgical instrument of the dilation instrument system may comprise a retraction mechanism operable to automatically retract the needle tip after the needle tip penetrates the lumen of the patient's trachea.

According to another aspect, a surgical instrument system comprising a catheter having a lumen defined therein, the catheter further including a distal tip formed from a first material and an elongated body extending from the distal tip to an opposite proximal end, the elongated body being formed from a second material that has a hardness greater than the first material.

According to another aspect, a method of dilating an opening in a patient's tissue is disclosed. The method comprises advancing a distal end of a balloon catheter in a first direction through the opening in the patient's tissue, pulling the balloon catheter in a second direction opposite the first direction to engage a retention flange secured to the distal end with an inner surface of the patient's tissue, advancing a retainer along the balloon catheter in the first direction to engage an outer surface of the patient's tissue opposite the inner surface, and inflating a balloon of the balloon catheter to dilate the opening in the patient's tissue.

According to another aspect, a method of dilating an opening in a patient's tissue comprises positioning an uninflated dilation balloon in the opening in the patient's tissue, engaging a retention flange with an inner surface of the patient's tissue, advancing a moveable retainer along the balloon to a position adjacent to an outer surface of the patient's tissue opposite the inner surface, and inflating the balloon to dilate the opening in the patient's tissue.

In some embodiments, the method may further comprise positioning an elongated shaft of a surgical instrument in a lumen defined in the balloon catheter such that a needle tip of the surgical instrument extends outwardly from the distal end of the balloon catheter, inserting the needle tip of the surgical instrument into the outer surface of the patient's tissue, and advancing the needle tip through the tissue to define the opening.

In some embodiments, the surgical instrument may be operable to automatically retract the needle tip into the lumen of the balloon catheter when the needle tip has penetrated the inner surface of the tissue.

In some embodiments, the method may further comprise monitoring an indicator of the surgical instrument while advancing the needle tip through the tissue. The surgical instrument may be operable to automatically retract the needle tip in response to the indicator indicating the needle tip has penetrated the inner surface of the tissue. Additionally, in some embodiments, the indicator may be operable to provide a visual indication when the needle tip has penetrated the inner surface of the tissue.

In some embodiments, advancing the retainer along the balloon catheter in the first direction may include engaging an annular body of the retainer with the outer surface of the tissue.

According to another aspect, a dilation instrument system is disclosed. The system comprises a balloon catheter configured to be positioned in an opening defined in a patient's tissue. The catheter includes a sheath having a proximal end and an elastomeric distal end, an inflatable balloon extending over the sheath between the proximal end and the distal end, and a deformable retention flange secured to the distal end of the sheath. The system also includes a retainer positioned over the balloon and configured to move relative to the balloon such that upon inflation of the balloon when the balloon is positioned in the opening in the patient's tissue, the retainer engages the patient's tissue to inhibit movement of the balloon catheter. The system also includes a surgical instrument removably coupled to the sheath. The surgical instrument comprises a needle tip extending outwardly from the sheath that is configured to puncture the patient's tissue. The surgical instrument may further comprise a retraction mechanism operable to automatically retract the needle tip after the needle tip penetrates a lumen of the patient's tissue. Additionally, the sheath may comprise a tip positioned at the distal end that is formed from a first material, and an elongated body extending from the tip to the proximal end of the sheath. The elongated body may be formed from a second material that is harder than the first material, and the retraction mechanism is operable to retract the needle tip into the tip of the sheath.

According to another aspect, a surgical instrument system comprises an elongated body including a handle and a shaft extending from the handle to a distal end configured to pass through a patient's tissue, an indicator, a sensor operable to generate an electrical signal, and a control circuit. The control circuit is configured to receive the electrical signal from the sensor, determine whether the distal end has penetrated a lumen of a patient, and activate the indicator when the distal end has penetrated the lumen of the patient.

In some embodiments, the control circuit may be configured to determine whether the distal end has engaged tissue of a patient, energize the light source in a first state when the distal end has engaged tissue of the patient, and energize the light source in a second state when the distal end has penetrated the lumen of the patient. The second state may be different from the first state. Additionally, when the light source is in the first state, the light source may be flashing.

In some embodiments, the system may further comprise a retraction mechanism operable to retract the distal end. The control circuit may be configured to energize the retraction mechanism when the distal end has penetrated the lumen of the patient.

In some embodiments, the retraction mechanism may include a biasing element configured to bias the distal end in a retracted position. In some embodiments, the retraction mechanism may include a locking arm configured to maintain the distal end in an extended position.

In some embodiments, the control circuit may be configured to determine whether the distal end has engaged tissue of a patient, energize the light source in a first state when the distal end has engaged tissue of the patient, and energize the light source in a second state when the distal end has penetrated the lumen of the patient, the second state being different from the first state. In some embodiments, the system may further comprise a retraction mechanism operable to retract the distal end. The control circuit may be configured to energize the retraction mechanism when the distal end has penetrated the lumen of the patient.

In some embodiments, the sensor may include an outer surface of the shaft electrically connected to the control circuit and a first plate positioned at the distal end of the shaft. The first plate may be electrically connected to the control circuit.

Additionally, in some embodiments, the control circuit may be operable to apply an electrical charge to the first plate. In some embodiments, the sensor may be operable to measure changes in electrical properties of the patient's tissue.

In some embodiments, the sensor may be operable to measure changes in resistance.

According to another aspect, a method for performing a surgical procedure comprises inserting a needle tip of a surgical instrument into a patient's tissue, advancing the needle tip through the tissue, monitoring an indicator of the surgical instrument while advancing the needle tip through the tissue, and maintaining a position of the surgical instrument in response to the indicator indicating the needle tip has entered a target lumen of the patient.

In some embodiments, the surgical instrument may be operable to automatically retract the needle tip when the needle tip has entered the target lumen of the patient. Additionally, in some embodiments, the surgical instrument may include a control circuit operable to measure a change in electrical properties to determine when the needle tip has entered the target lumen of the patient and activate the indicator to indicate the needle tip has entered a target lumen of the patient.

In some embodiments, the surgical instrument may be operable to apply an electrical charge to a plate positioned at the needle tip. In some embodiments, the control circuit may be operable to determine when the needle tip has entered the target lumen of the patient based on a change in electrical resistance.

In some embodiments, the control circuit may be operable to determine when the needle tip has entered the target lumen of the patient based on a change in resistance. In some embodiments, the target lumen may be devoid of liquid and/or tissue. In some embodiments, liquid may be present in the target lumen.

According to another aspect, a surgical instrument system configured to perform any of the methods described herein is disclosed.

BRIEF DESCRIPTION OF THE DRAWINGS

The detailed description particularly refers to the following figures, in which:

FIG. 4A is a partial cross-section elevation view of a detail of FIG. 4;

DETAILED DESCRIPTION OF THE DRAWINGS

Figure 1:
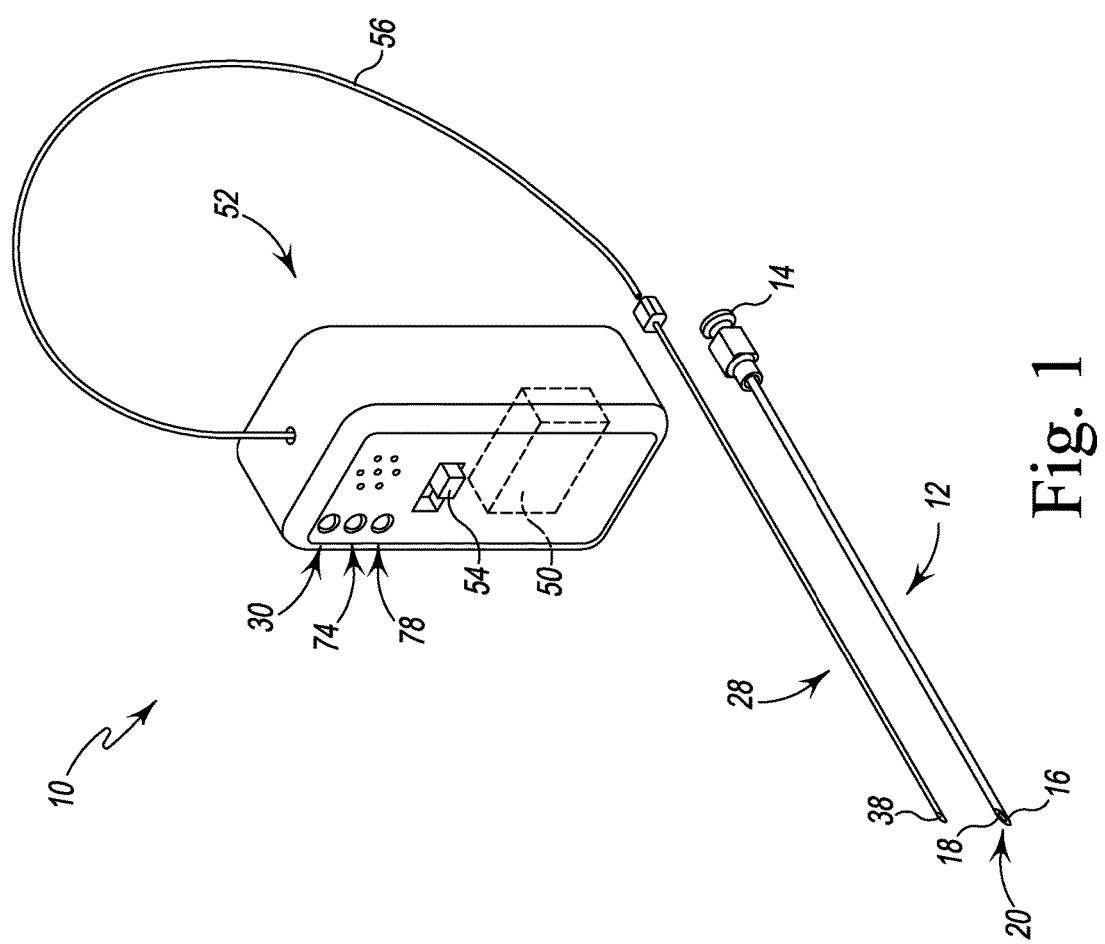
FIG. 1 is a perspective view of one embodiment of a surgical instrument system for use in performing a surgical procedure.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Figure 2:
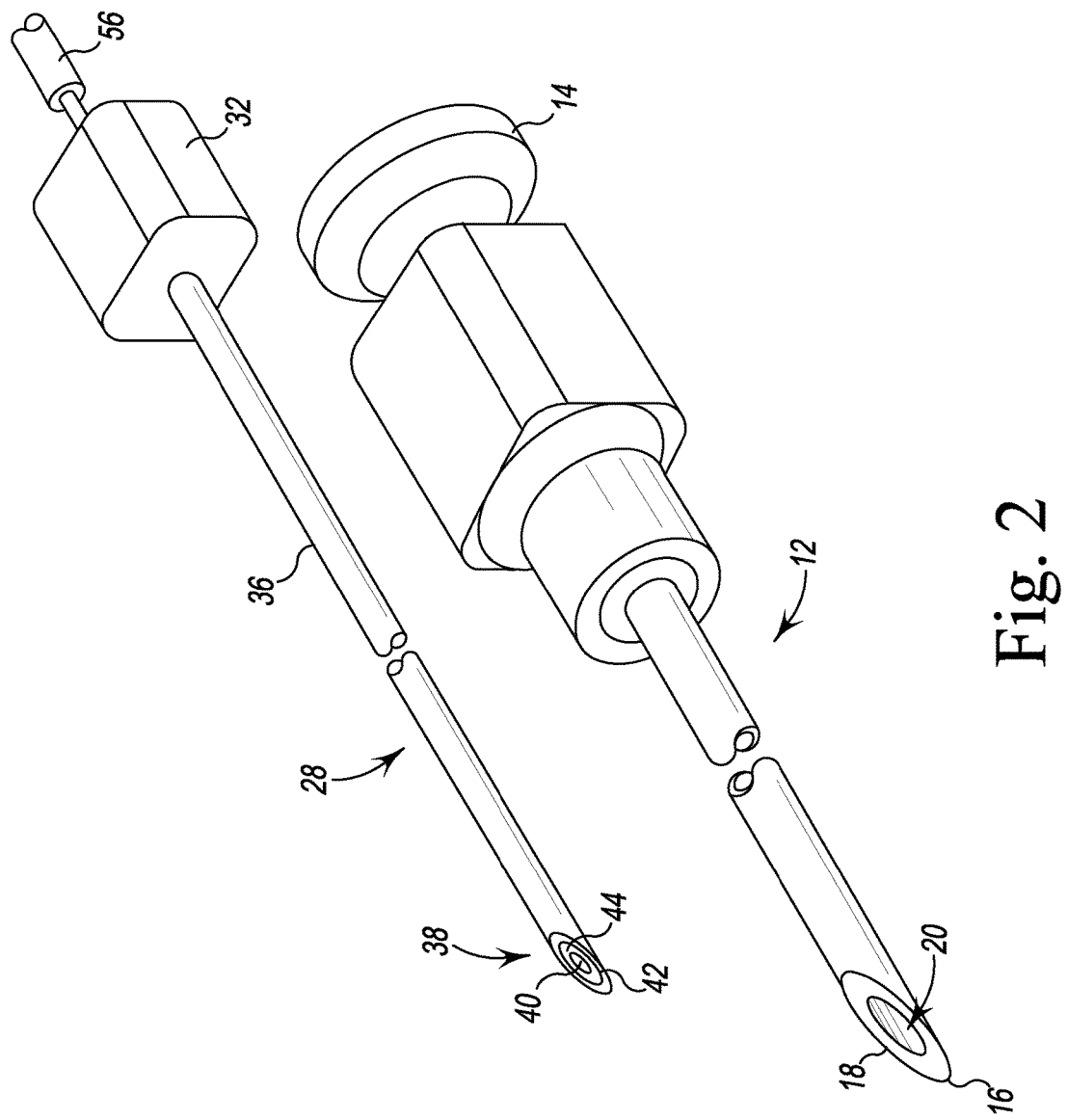
FIG. 2 is a perspective view of some of the components of the system of FIG. 1.
Figure 3:
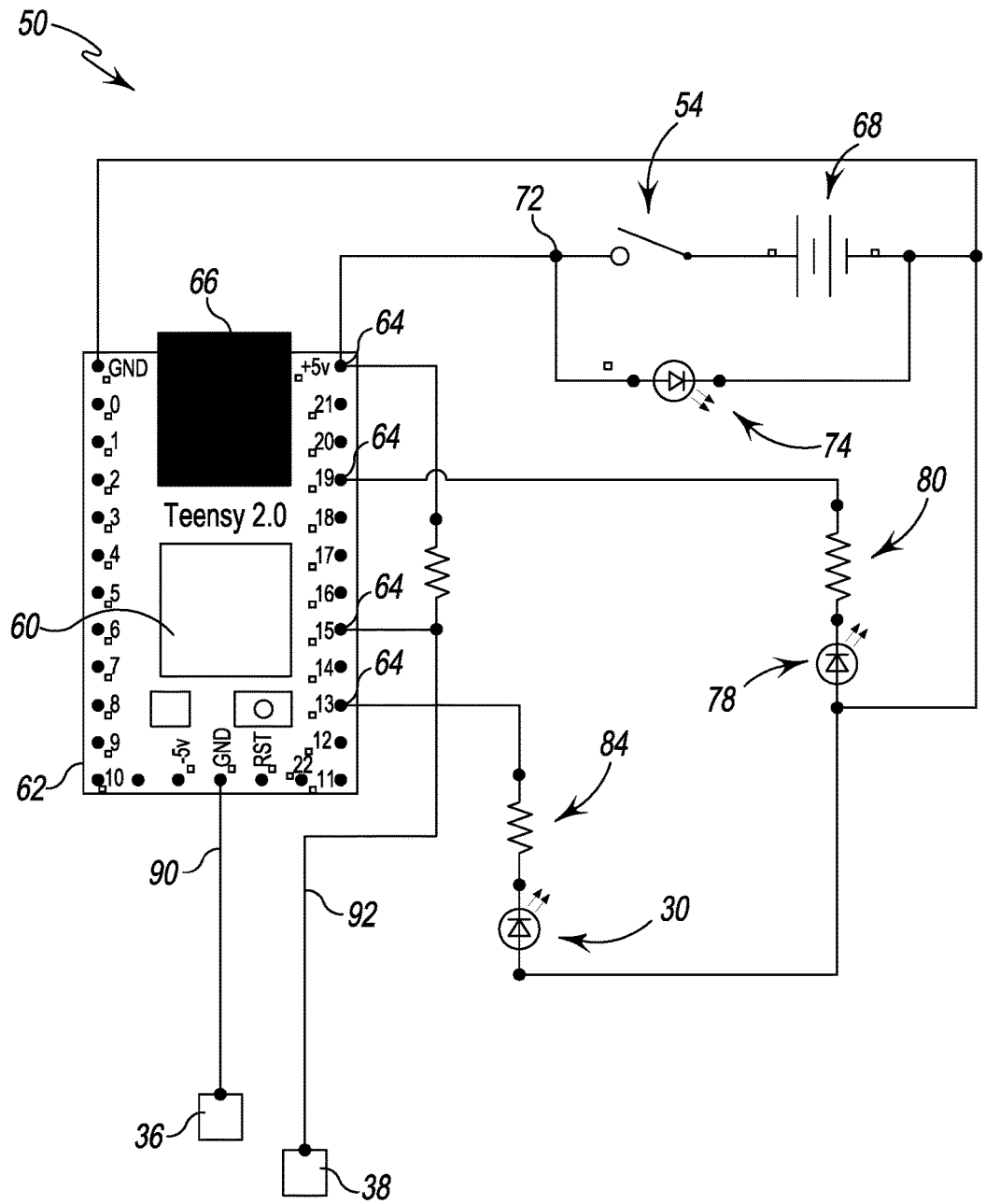
FIG. 3 illustrates a circuit diagram of an electrical circuit of the surgical instrument system of FIG. 1.

Referring now to FIGS. 1-3, a surgical instrument system 10 configured for insertion into the soft tissue of a patient is illustrated. Illustratively, the surgical instrument 10 may be use to form a puncture between the skin of the neck and the anterior wall of the trachea of a patient, but it should be appreciated that the surgical instrument 10 may be used to form other punctures, incisions, or openings in the patient's tissue. The surgical instrument system 10 includes an elongated needle body 12 that extends from a proximal end 14 to a distal end 16. A needle tip 18 configured to pierce the tissue is formed at the distal end 16 of the body 12. The needle body 12 has a lumen or passageway 20 extending through the ends 14, 16, as shown in FIG. 2. In the illustrative embodiment, a catheter may be inserted into the passageway 20 to provide, for example, epidural anesthesia, to a patient. The surgical instrument system 10 also includes a probe 28 that is sized to be positioned in the passageway 20 of the needle 12. The probe 28 is connected to an indicator 30 that is configured to notify a user that the needle tip 18 has penetrated the tissue, as described in greater detail below.

The probe 28 includes a base 32 and a shaft 36 that extends distally away from the base 32 to a tip 38. In the illustrated embodiment, the shaft 36 is a cannula formed from an electrically conductive material. The tip 38 and the shaft 36 are integral, but it should be appreciated that in other embodiments the tip 38 and the shaft 36 may be formed as separate components and assembled. As shown in FIG. 2, the probe 28 includes a conductor plate 40 that is positioned in the distal opening 42 of the tip 38. In the illustrative embodiment, the plate 40 is electrically insulated from the tip 38 by a non-conductive film 44. In the illustrative embodiment, the film 44 is a ring having a predetermined thickness that surrounds the plate 40. In other embodiments, the shaft may be formed from a non-conductive material such as ceramic or plastic to insulate the plate. The plate 40 and the film 44 cooperate to cover the opening 42 such that fluid is prevented from entering the tip 38. When a patient's tissue contacts the conductor plate 40, electrical circuitry 50 of the system 10 is operable to detect the change in electrical resistance caused by the contact with the tissue, as described in greater detail below.

Returning to FIG. 1, the system 10 includes a control box 52 that houses the electrical circuitry 50, including the indicator 30. In the illustrative embodiment, the control box 52 has a power switch 54 that may be toggled to energize the electrical circuitry 50. A cable 56 connects the electrical circuitry 50 with the probe 28.

Referring now to FIG. 3, the electrical circuitry 50 for the system 10 is shown in greater detail. In the illustrative embodiment, the circuitry 50 is operable to detect a change in electrical resistance that is produced when the probe tip 38 exits one type of tissue and enters another type of tissue or lumen, as described in greater detail below.

The circuitry 50 includes a microprocessor 60 such as, for example, an 8-Bit AVR 16 MHz Processor (ATMEGA32U4) commercially available from Atmel Corporation. The microprocessor 60 is attached a circuit 62 that also includes various terminals 64 connected to other circuitry 50. An I/O port 66 such as, for example, a USB port, is attached to the circuit 62 to permit a user to upload software and data to, and download from, the microprocessor 60. Illustratively, the microprocessor 60, the circuit 62, and the I/O port 66 are available in a Teensy 2.0 USB-based microcontroller development system. A voltage supply includes two 3 VDC batteries 68, the anodes of which are coupled to one terminal 70 of the power switch 54. The other terminal 72 of switch 54 is coupled to the 5V terminal of the circuit 62 and to the anode of a "Power Indicator" LED 74. The cathode of the Power Indicator LED 74 is coupled to the cathodes of the batteries 68 and to the GrouND terminal of the circuit 62 at the terminal 76.

The circuitry 50 also includes a "Low Battery" LED 78, which is energized by the microprocessor 60 when battery voltage drops below a predetermined threshold. The cathode of the LED 78 is connected through a 220 Ω resistor 80 to the "19" terminal of the circuit 62. The anode of the LED 78 is connected to the GrouND terminal of the circuit 62 and an anode of the indicator LED 30. The cathode of the LED 30 is connected to the "13" terminal of the circuit 62 through another 220 Ω resistor 84.

The shaft 36 of the probe 28 is coupled via a wire 90 to a ground terminal of the circuit 62. The conductor plate 40 of the tip 38 is coupled via a wire 92 through a 4.7 kΩ resistor to the "15" terminal and the 5V terminal of the circuit 62.

Illustratively, the microprocessor 60 applies 4.7V dc to the conductor plate 40 while the shaft 36 is connected to ground. The microprocessor 60 is programmed to measure the resistance received by the circuit 62 at a controlled distance. In the illustrative embodiment, the distance is equal to a 0.5 millimeter gap between the conductor plate 40 and the cutting end of the shaft 36 that is created by the film 44. In the illustrative embodiment, the 0.5 millimeter gap corresponds to the thickness of the film ring 44. When the conductor plate 40 exits the patient's tissue and enters a liquid-filled or empty target lumen, the resistance sensed at the conductor plate 40 experiences a "step" change, which the microprocessor 60 is programmed to register as indicating, for example, that the tip 38 has penetrated a lumen. The microprocessor 60 is programmed to switch the "13" terminal continuously "high," thereby turning the indicator LED 30 continuously "on."

When the probe tip 38 engages the patient's tissue, the resistance experienced by circuit changes. In the illustrative embodiment, the microprocessor 60 is programmed to consecutively toggle the "13" terminal "high" and "low," thereby causing the LED 30 to flash "on" and "off" to indicate to the user that the instrument system 10 is armed. As the needle 12 (and hence the probe 38) is advanced into the spinal column, the conductor plate 40 remains engaged with the patient's tissue.

When the probe tip 38 reaches, and protrudes into, the target lumen (e.g., the interior of a patient's spinal column or trachea), the electrical resistance in the circuit changes sharply, and the microprocessor 60 is programmed to switch the "13" terminal continuously "high," thereby turning the indicator LED 30 continuously "on" to inform the user to hold the needle 12 in position. The user may then remove the probe 28 from the lumen 20 of the needle 12 while leaving the needle 12 inserted into the patient's tissue. The user may then use the lumen 20 to position, for example, a catheter to provide fluids to the patient.

Figure 4:
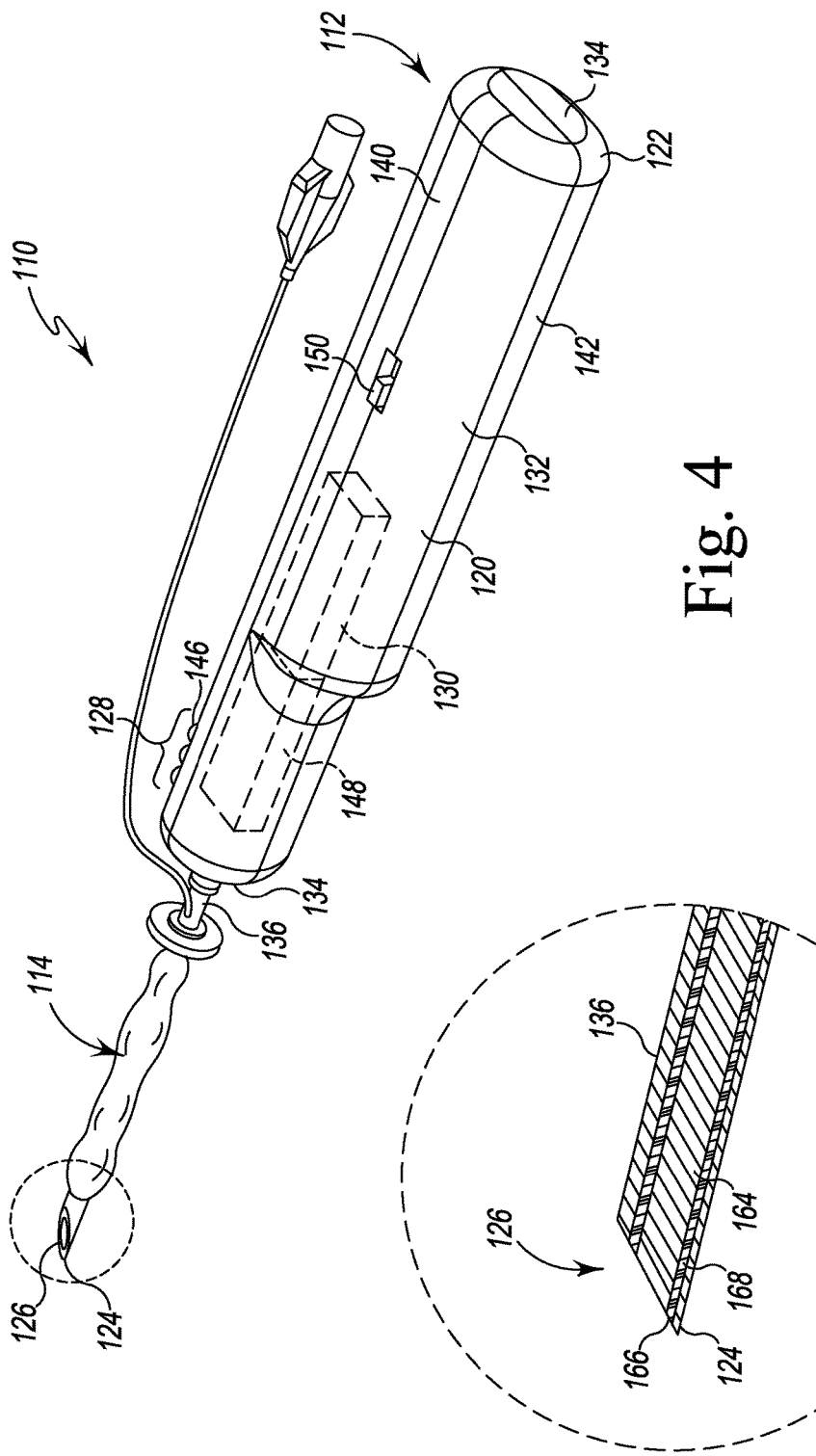
FIG. 4 is a perspective view illustrating another surgical instrument system.

Referring now to FIG. 4, another instrument system 110 configured for insertion into the soft tissue of a patient is illustrated. The system 110 is also configured for forming and dilating an opening in a patient's tissue is shown. The instrument system 110 includes a puncture instrument 112 and a balloon catheter 114 that is removably coupled to the puncture instrument. An exemplary balloon catheter for use in the system 110 is shown and described in U.S. patent application Ser. No. 14/996,426, which is expressly incorporated herein by reference. The instrument system 110 may be used, for example, to create a puncture or incision in a tracheal wall of a patient and dilate the incision to receive a prosthesis such as, for example, a tracheostomy tube to form an air passageway for the patient. For convenience, the balloon catheter 114 is not shown in the illustrations of FIGS. 5-10.

Illustratively, the puncture instrument 112 may be used to form a puncture between the skin of the neck and the anterior wall of the trachea of a patient, but it should be appreciated that the puncture instrument 112 may be used to form other punctures, incisions, or openings in the patient's tissue. As shown in FIG. 4, the puncture instrument 112 includes an elongated body 120 having a proximal end 122 and a distal end 124. A needle tip 126 configured to pierce the tissue is formed at the distal end 124 of the body 120. As described in greater detail below, the puncture instrument 112 also includes an indicator 128 configured to notify a user that the needle tip 126 has penetrated the tissue and an automatic needle retraction mechanism 130 operable quickly to retract the needle tip 126 a short distance after the needle tip 126 has penetrated the tissue.

The elongated body 120 includes a handle 132 extending from the proximal end 122 to a distal handle end 134. A shaft 136 extends distally away from the handle 132 to the needle tip 126. In the illustrated embodiment, the shaft 136 is a cannula formed from a metallic material. In other embodiments, the shaft may be formed from a ceramic or plastic material. The needle tip 126 and the shaft 136 are integral, but it should be appreciated that in other embodiments the needle tip 126 and the shaft 136 may be formed as separate components and assembled.

The handle 132 illustratively includes an upper housing 140 that is configured to be coupled to a lower housing 142. The indicator 128 includes a light source such as, for example, a plurality of light emitting diodes (LED) 146 that is illustratively visible through an opening in the upper housing 140. The housings 140, 142 cooperate to define a chamber in which other electrical circuitry 148 is positioned. The circuitry 148 is operable to energize the LED 146 to provide a visual output to the user. In other embodiments, the indicator 128 may include other electrical circuitry to provide an audible output to the user. The puncture instrument 112 also includes a power switch 150, which is operable to supply power to the electrical circuitry 148 including LEDs 146.

Figure 5:
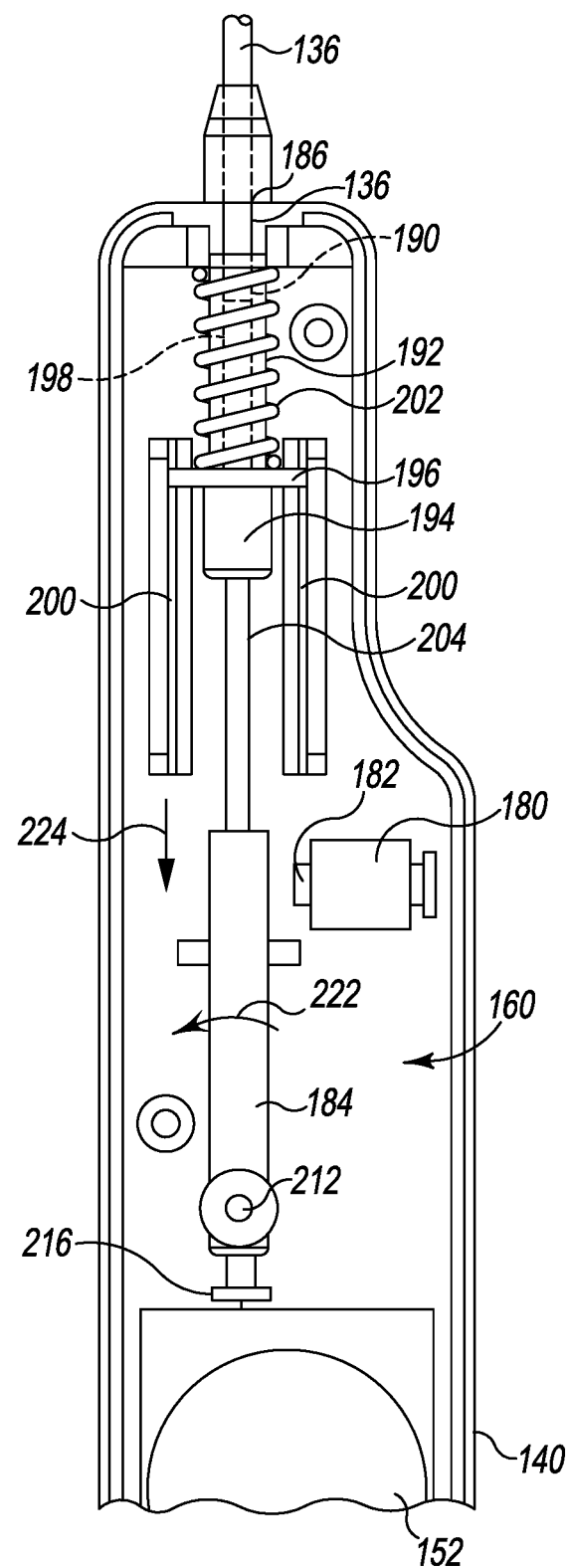
FIGS. 5-6 are partial cross-sectional plan views of a surgical instrument of the instrument system of FIG. 4.

As shown in FIG. 5, the electrical circuitry 148 includes a battery pack 152 positioned at one end of the handle 132 and the automatic needle retraction mechanism 160, which is operable to retract the needle tip 126 a short distance after the needle tip 126 has penetrated the tissue. In illustrative embodiment, the distance is 8 millimeters. A metallic plate (not shown) is positioned in handle 132 is formed from copper and is configured to provide a ground plane for the electrical circuitry 148, which makes the user the ground for the electrical circuitry.

Returning to FIG. 4A, the instrument 112 also includes a conductor plate 164 that is positioned in the distal opening 166 of the needle tip 126. In the illustrative embodiment, the plate 164 is a metallic shaft that is electrically insulated from the needle tip 126 by a non-conductive film 168. In the illustrative embodiment, the film 44 is a cylindrical ring having a predetermined thickness that surrounds the plate 40. In other embodiments, the needle tip and/or needle shaft may be formed from a non-conductive material such as, for example, ceramic or plastic to electrically insulate the plate. The shaft 164 and the film 168 cooperate to cover the opening 166 such that fluid is prevented from entering the needle tip 126. A wire or conductor 170 connects the shaft 164 to the electrical circuitry 148, and another wire or conductor 172 connects the outer cannula shaft 136 to the electrical circuitry 148. When a patient's tissue contacts the conductor plate 164, the electrical circuitry 148 is operable to detect the change in electrical resistance caused by the contact with the tissue, as described in greater detail below.

As described above, the instrument 112 includes an automatic needle retraction mechanism 160 operable to retract the needle tip 126 a short distance after the needle tip 126 has penetrated the tissue. As shown in FIG. 5, the needle retraction mechanism 160 includes an actuator 180. In the illustrative embodiment, the actuator 180 is a linear actuator such as, for example, a solenoid, which includes an output shaft 182 operable to move along a straight line. An exemplary actuator is the Uxcell a14092600ux0438 Open Frame Actuator, which is electrically-operated. In other embodiments, the actuator may be embodied as an electric motor, electromagnet, or other electromechanical device operable to move the locking arm 184, as described in greater detail below. As shown in FIG. 5, the locking arm 184 that maintains the needle shaft 136 in an extended position.

Figure 6:
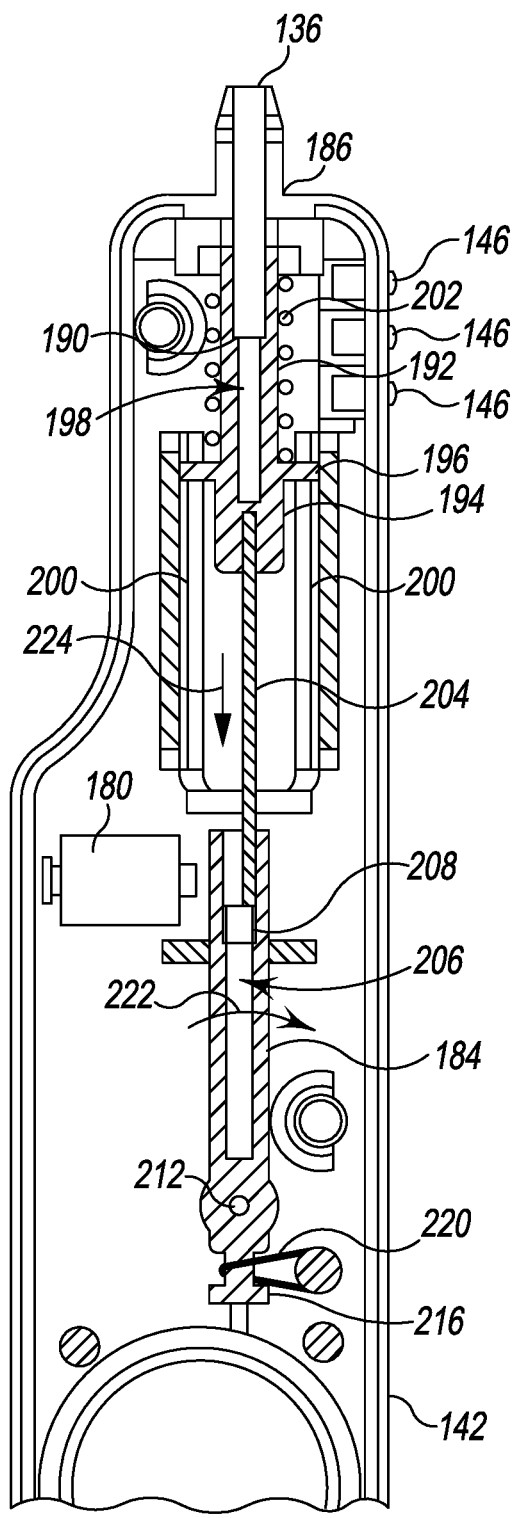

The needle shaft 136 extends through an opening 186 defined in the distal handle end 134, and the shaft 136 includes a proximal end 190 that is secured to a mounting bracket 192 positioned in the handle 132. The mounting bracket 192 includes a cylindrical body 194 and a slide plate 196 that extends outwardly from the body 194. As shown in FIG. 6, an aperture 198 is defined at one end of the cylindrical body 194, which receives the proximal end 190 of the shaft 136 and provides a passageway through which the connecting wire 170 passes to connect the conductor plate 164 to the other electrical circuitry 148.

As shown in FIG. 5, the edges of the slide plate 196 are received in a pair of guide slots 200 defined in the handle 132, which guide the movement of the mounting bracket 192 as the needle tip 126 is retracted. A biasing element such as, for example, a spring 202 positioned between the slide plate 196 and the distal handle end 134. In the illustrative embodiment, the spring 202 is configured to bias the slide plate 196 away from the distal handle end 134 and hence bias the needle tip 126 is the retracted position.

A rod 204 extends between the cylindrical body 194 and the locking arm 184. As shown in FIG. 6, the rod 204 is received in an aperture 206 defined in the locking arm 184. The locking arm 184 includes a sleeve 208 positioned in the aperture 206, and the rod 204 engages the sleeve 208 when the needle shaft 136 is an extended position. In the illustrative embodiment, the sleeve 208 is formed from a metallic material such as, for example, steel. A pivot pin 212 extends outwardly from the lower housing 142 and is received in a bore defined in the locking arm 184 near an end 216. The retraction mechanism 160 also includes another biasing element, illustratively embodied as an elastic band 220, which is coupled to the shaft end 216 and the lower housing 142.

When the needle shaft 136 is in its extended position and ready for insertion into a patient's tissue, the sleeve 208 is initially engaged with the rod 204, as shown in FIG. 6. The band 220 applies a force to the locking arm 184 to bias in the position shown in FIG. 6 to keep the rod 204 engaged with the sleeve 208, thereby resisting the force exerted by the spring 202 against the slide plate 196 and maintaining the needle shaft 136 in the extended position.

As described above, the automatic needle retraction mechanism 130 is operable to quickly retract the needle tip 126 a short distance after the needle tip 126 has penetrated the tissue. To do so, the linear actuator 180 is energized to advance its shaft 182 into contact with the locking arm 184, thereby causing the arm 184 to pivot about the pin 212 as indicated by arrow 222. As the arm 184 pivots, the end of the rod 204 disengages from the sleeve 208 and moves toward the center of the aperture 206. When the rod 204 disengages from the sleeve 208, the spring 202 urges the mounting bracket 192 in the direction indicated by arrow 224 in FIG. 6. As the mounting bracket 192 moves, the needle tip 126 retracts away from the opposite wall of the patient's lumen.

Figure 7:
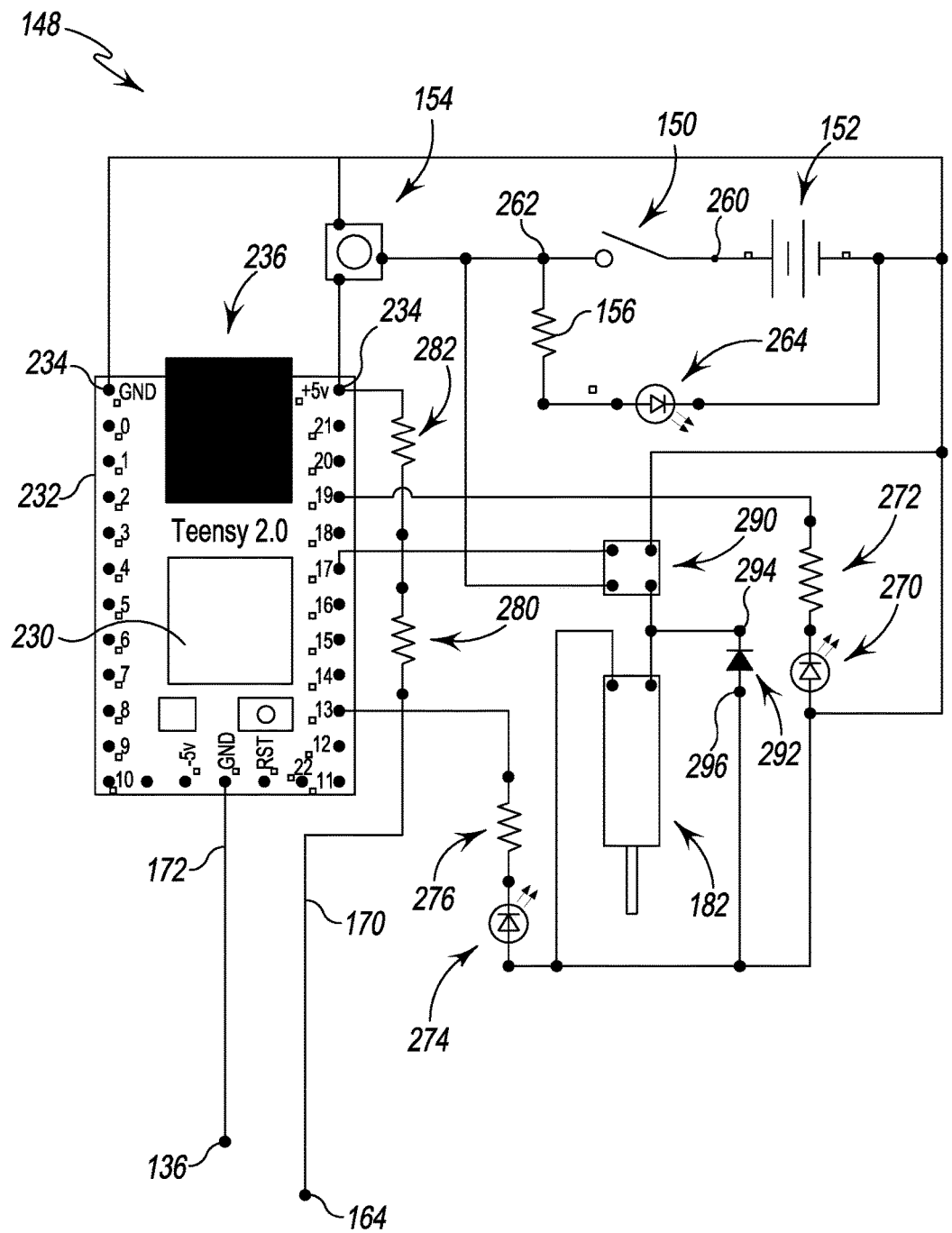
FIG. 7 is a circuit diagram of an electrical circuit of the surgical instrument system of FIG. 4.

Referring now to FIG. 7, the electrical circuitry 148 is shown. As described above, the electrical circuitry 148 is operable to detect a change in electrical resistance that is produced when the needle tip 126 exits one type of tissue and enters another type of tissue or lumen, as described in greater detail below. In that way, the electrical circuitry 148 functions as a sensor.

The circuitry 148 includes a microprocessor 230 such as, for example, an 8-Bit AVR 16 MHz Processor (ATMEGA32U4), which is commercially available from Atmel Corporation. The microprocessor 230 is attached a circuit 232 that also includes various terminals 234 connected to other circuitry 148. An I/O port 236 such as, for example, a USB port, is attached to the circuit 232 to permit a user to upload software and data to, and download from, the microprocessor 230. Illustratively, the microprocessor 230, the circuit 232, and the I/O port 236 are available in a Teensy 2.0 USB-based microcontroller development system. A voltage supply includes a single 9 VDC battery 152, the anode of which is coupled to one terminal 260 of the power switch 150. The other terminal 262 of switch 150 is coupled to a voltage regulator 154 and to the anode of a "Power Indicator" LED 264 of the LEDs 146 through a 220 Ω resistor 156. As shown in FIG. 7, the cathode of the Power Indicator LED 264 is coupled to the cathode of the battery 152 and to the GrouND terminal of the circuit 232. In the illustrative embodiment, the voltage regulator 154 is a Texas Instruments LP2981 regulator. The voltage regulator 154 is connected to the 5V terminal of the circuit 232 and is configured to condition the 9 VDC battery voltage to 5 volts.

The circuitry 148 also includes a "Low Battery" LED 270, which is energized by the microprocessor 230 when battery voltage drops below a predetermined threshold. The cathode of the LED 270 is connected through a 220 Ω resistor 272 to the "13" terminal of the circuit 232. The anode of the LED 270 is connected to the GrouND terminal of the circuit 232 and an anode of the penetration indicator LED 274. The cathode of the LED 274 is connected to the "13" terminal of the circuit 232 through another 220 Ω resistor 276. A battery monitor (not shown) may be connected to another terminal of the circuit 232.

The shaft 136 of the instrument 112 is coupled via a wire 172 to a ground terminal of the circuit 232. The conductor plate 164 in the tip 126 is coupled via a wire 170 through a 68 Ω resistor 280 and a 100 kΩ resistor 282 to the "18" terminal and the 5V terminal of the circuit 232. The shaft 136 and the plate 164 form part of the sensor circuit used to detect when the needle tip 126 has penetrated a lumen. It should be appreciated that in other embodiments the sensor circuit may include a pair of conductor plates, which are electrically isolated from one another, and the elongated shaft may be formed from a non-conductive material.

The linear actuator 180 is connected to the anodes of the LEDs 270, 274 and the GrouND terminal of the circuit 232. The linear actuator 180 is also connected to a relay switch 290, which is positioned between the actuator 180 and the terminal 262 of the switch 150. The relay switch 290 is also connected to the "17" terminal of the circuit 232 and to the GrouND terminal, as shown in FIG. 7. The circuitry 148 also includes a snubber diode 292 that is connected between the positive and negative poles of the actuator 180 and the power supply 152. As shown in FIG. 7, the cathode 294 of the diode 292 is connected to the relay switch 290, while the anode 296 of the diode 292 is connected to the linear actuator 180 and the power supply 152.

Illustratively, the microprocessor 230 applies 4.7 VDC to the conductor plate 164 while the shaft 136 is connected to ground (e.g., the user's hand). The microprocessor 230 is programmed to measure the electrical resistance in the circuit 232 at a controlled distance. In the illustrative embodiment, the distance is equal to a 0.5 millimeter gap between the conductor plate 164 and the cutting end of the shaft 136 that is created the non-conductive film 168. In the illustrative embodiment, the 0.5 millimeter gap corresponds to the thickness of the film ring 168. During operation, when the conductor plate 164 exits the patient's tissue and enters a liquid-filled or empty target lumen, the resistance sensed at the conductor plate 164 experiences a "step" change, which the microprocessor 230 is programmed to register as indicating, for example, that the tip 126 has penetrated a lumen. The microprocessor 230 is programmed to switch the "13" terminal continuously "high," thereby turning the indicator LED 274 continuously "on."

Figure 8:
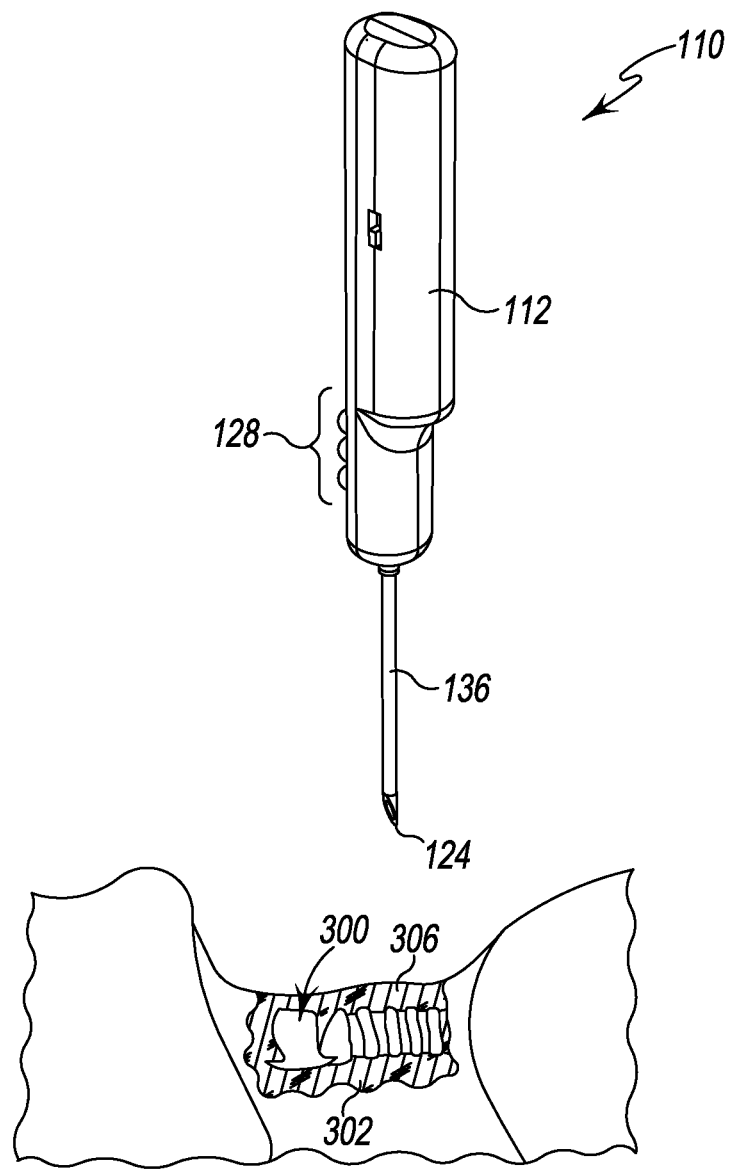
FIG. 8 is a side elevation view of the surgical instrument of FIGS. 4-7 positioned for insertion into a patient's soft tissue.

In use, the needle tip 126 of the surgical instrument 112 may be used to form a puncture in a patient's issue. As shown in FIG. 8, a surgeon or other user may align the needle tip 126 with the target lumen of the patient's body (in this case, a patient's trachea 300) and toggle the power switch 150 to energize the sensor circuit formed by the microprocessor 230, the conductor shaft 164, and the outer cannula 136. Initially, when the needle tip 126 is out of contact with the patient's tissue, the circuit is open and the resistance value effectively infinite.

Once the needle tip 126 is properly aligned, it may be advanced into contact with the patient's tissue and through the anterior wall 306. When the needle tip 126 engages the patient's tissue, the circuit is closed, and the resistance value measured by the microprocessor 230 enters a predetermined range. In the illustrative embodiment, the range is between 1 kilo-ohm and 100 kilo-ohms. It should be appreciated that in other embodiments other ranges of resistance values may be used. The controller 230 activates a timer when the resistance value enters the predetermined range, and after a predetermined amount of time, the microprocessor 230 activates the LED 274. In the illustrative embodiment, the predetermined amount of time is 200 milliseconds. When the microprocessor 230 activates the LED 274 in the illustrative embodiment, the microprocessor 230 is programmed to consecutively toggle the "13" terminal "high" and "low," thereby causing the LED 274 to flash "on" and "off" to indicate to the user that the instrument 112 is armed.

In other embodiments, other sensors may be used to determine when the instrument 112 is properly positioned and ready to be armed. For example, the instrument 112 may include a pressure sensor that measures the pressure on the needle tip such that when the pressure surpasses the amount of pressure associated with penetrating the patient's tissue, the controller would activate the indicator and arm the instrument 112. In other embodiments, the instrument 112 may also include a cancel switch that the user may toggle to disarm the instrument 112.

Figure 9:
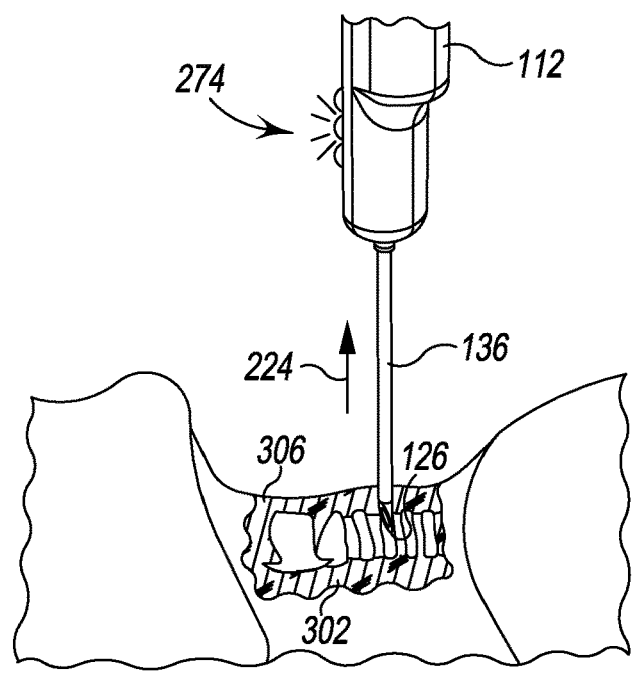
FIG. 9 illustrates the surgical instrument of FIGS. 4-7 as it enters a lumen of the patient.

As the needle 126 is advanced into the target lumen, the conductor plate 164 remains engaged with the patient's tissue. When the needle 126 reaches, and protrudes into, the target lumen (e.g., the trachea 300, esophagus, or spinal column) as shown in FIG. 9, the resistance at the conductor plate 164 changes sharply. In the case of a trachea, the sensor circuit effectively opens. When the resistance value passes a predetermined threshold, and the microprocessor 230 is programmed to switch the "13" terminal continuously "high," thereby turning the indicator LED 274 continuously "on" to inform the user that the needle 126 has reached the lumen. In the illustrative embodiment, the threshold is 100 kilo-ohms or greater.

Figure 10:
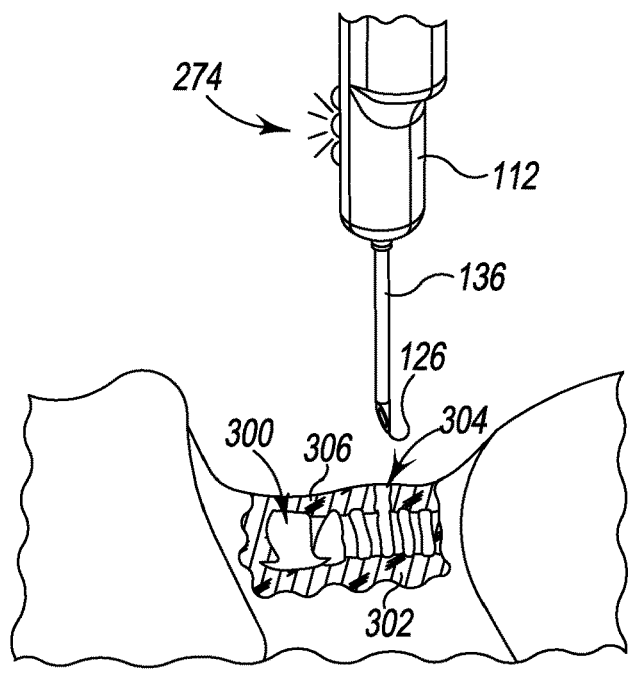
FIG. 10 illustrates the surgical instrument of FIGS. 4-7 after the needle of the surgical instrument has been retracted.

The microprocessor 230 is also programmed to switch the "17" terminal to "high" after a preset delay, thereby activating the relay switch 290. It should be appreciated that in other embodiments the preset delay may be omitted and the switch 290 activated immediately. When the switch 290 is activated, it connects the linear actuator 180 to the battery 152, thereby energizing the actuator. As described above, the actuator 180 is operable to advance its output shaft 182 into contact with the locking arm 184 and causing the locking arm 184 to pivot. As the arm 184 pivots, the end of the rod 204 disengages from the sleeve 208 and moves toward the center of the aperture 206. When the rod 204 disengages from the sleeve 208, the spring 202 urges the mounting bracket 192 in the direction indicated by arrow 224 in FIG. 6. As the mounting bracket 192 moves, the needle tip 126 retracts in direction shown in FIG. 9, away from the opposite wall 302 of the patient's trachea 300 and out of the incision 304, as shown in FIG. 10.

In other embodiments, the actuator may be embodied as an electric motor, electromagnet, or other electromechanical device operable to move the locking arm 184 within a sufficient period of time after the microprocessor detects penetration of the lumen. In the illustrative embodiment, the actuator 180 is operable to move the locking arm 184 such that the needle is retracted in 100 milliseconds.

Figure 11:
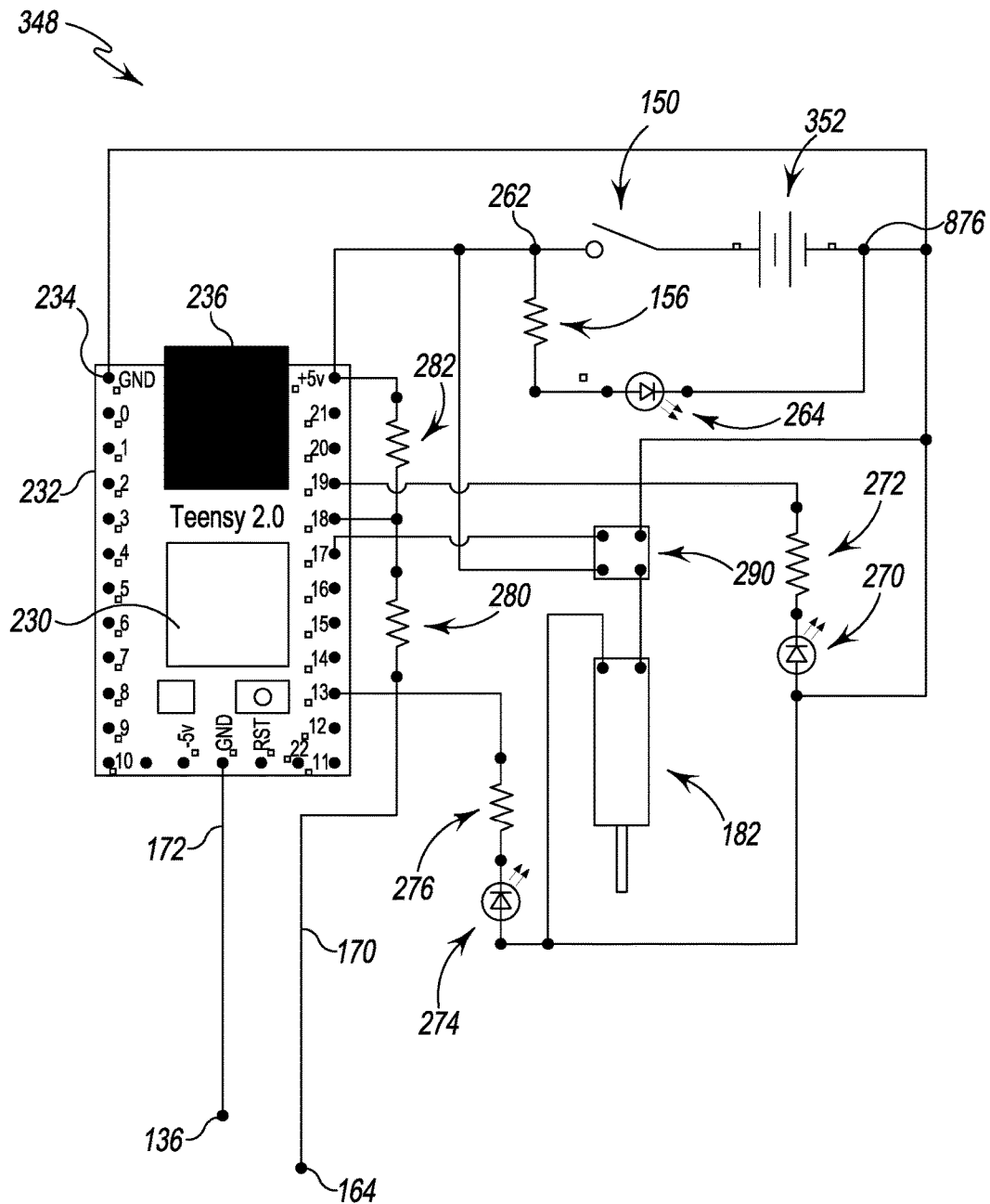
FIG. 11 is a circuit diagram of an electrical circuit for the surgical instrument system of FIG. 4.

Referring now to FIG. 11, another embodiment of electrical circuitry 348 is illustrated. The electrical circuitry 348 is identical to the circuitry 148 described above, except for the use of two 3 VDC batteries and the omission of a voltage regulator and snubber diode. As shown in FIG. 11, the anodes of the two 3 VDC batteries 352 are coupled to one terminal 260 of the power switch 150. The other terminal 262 of switch 150 is coupled to the 5V terminal of the circuit 232 and to the anode of the "Power Indicator" LED 264 of the LEDs 146.

It should be appreciated that although the concept of detecting a lumen in a patient's body has been described above in reference to surgical instruments that may be used to create punctures in a patient's tissue, the techniques and concepts described above may be incorporated into other surgical instruments such that entry into a lumen or movement between various tissue types may be detected. For example, any surgical cutting tool such as, for example, a cutting blade, reamer, drill, or other instrument may include circuitry to detect fluctuating levels of electrical resistance and thereby determine when a distal end of the cutting tool has entered a lumen. Other surgical instruments such as, for example, guides, trials, probes, and so forth may also include circuitry to detect fluctuating levels of electrical resistance and thereby determine when a distal end of the surgical instrument has entered a lumen.

While the disclosure has been illustrated and described in detail in the drawings and foregoing description, such illustration and description is to be considered as exemplary and not restrictive in character, it being understood that only illustrative embodiments have been illustrated and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical instrument system comprising:
   a housing including a handle,
   a shaft extending outwardly from the housing to a distal end configured to form a puncture in a patient's tissue,
   a conductor plate positioned in the shaft,
   a retraction mechanism operable to move the distal end of the shaft in a first direction toward the housing, and
   a controller positioned in the housing, the controller being configured to: (i) energize a sensor circuit including a section of the shaft and the conductor plate, and (ii) monitor an electrical signal received from the sensor circuit,
   wherein when an electrical resistance value based on the monitored electrical signal is greater than a predetermined threshold, the controller is configured to: (i) activate an indicator, and (ii) energize the retraction mechanism to move the distal end of the shaft in the first direction toward the housing.

2. The surgical instrument system of claim 1, wherein the predetermined threshold for the resistance value is greater than or equal to 100 kilo-ohms.

3. The surgical instrument system of claim 1, wherein the conductor plate is positioned in an opening defined in the distal end of the shaft.

4. The surgical instrument system of claim 3, further comprising a non-conductive film positioned in the opening defined in the distal end of the shaft between the conductor plate and the shaft that electrically isolates the conductor plate from the shaft.

5. The surgical instrument system of claim 4, wherein the non-conductive film includes an annular ring that surrounds the conductor plate.

6. The surgical instrument system of claim 5, wherein the annular ring has a thickness of 0.5 millimeters.

7. The surgical instrument system of claim 1, wherein the indicator is a visual indicator.

8. The surgical instrument system of claim 1, wherein the controller is configured to:
  determine whether the distal end has engaged the patient's tissue based on the electrical signal received from the sensor circuit,
  energize the indicator in a first state when the controller has determined that the distal end has engaged the patient's tissue, and
  energize the indicator in a second state to activate the indicator when the controller has determined that the distal end has penetrated a lumen of the patient, the second state being different from the first state.

9. The surgical instrument system of claim 8, wherein when the resistance value based on the monitored electrical signal is less than a predetermined value for a predetermined period of time, the controller is configured to energize the indicator in the first state.

10. The surgical instrument system of claim 9, wherein the predetermined value is in a range of 1 kilo-ohm to 100 kilo-ohms.

11. The surgical instrument system of claim 9, wherein predetermined period of time is equal to 200 milliseconds.

12. The surgical instrument system of claim 8, wherein:
  the first state is one of a flashing light and a continuous light, and
  the second state is the other of a flashing light and a continuous light.

13. The surgical instrument system of claim 1, wherein the retraction mechanism includes a linear actuator.

14. The surgical instrument system of claim 13, wherein:
  the shaft is operable to move along a first axis, and
  the linear actuator is operable to move along a second axis extending orthogonal to the first axis to cause the shaft to move along the first axis.

15. The surgical instrument system of claim 1, wherein the shaft extends from the distal end to a proximal end positioned in the housing, and the retraction mechanism includes a mounting frame secured to the proximal end of the shaft.

16. The surgical instrument system of claim 15, wherein the retraction mechanism further includes a locking arm operable to rotate about a pivot pin between (i) a first position in which a proximal end of the mounting frame is engaged with a first surface of the locking arm and (ii) a second position in which the proximal end of the mounting frame is received in a passageway defined in the shaft.

17. The surgical instrument system of claim 16, further comprising a biasing element attached to an end of the locking arm, the biasing element being operable to bias the locking arm in the first position.

18. The surgical instrument system of claim 16, wherein the mounting frame includes a mounting bracket that has a first end secured to the shaft and a second, opposite end secured to an elongated rod, and the elongated rod includes the proximal end of the mounting frame.

19. The surgical instrument system of claim 18, wherein the locking arm includes a sleeve that includes the first surface.

20. The surgical instrument system of claim 15, further comprising a biasing element operable to urge the shaft in the first direction, wherein the biasing element is positioned between a plate of the mounting frame and a wall of the housing.

* * * * *